(12) United States Patent
Iwawaki (10) Patent No.: US 7,585,677 B2
(45) Date of Patent: Sep. 8, 2009

(54) METHOD OF EVALUATING CORROSION RESISTANCE OF MATERIAL UNDER AMMONIUM BISULFIDE ENVIRONMENT

(75) Inventor: Hirohito Iwawaki, Chiba (JP)

(73) Assignees: Petroleum Energy Center, Tokyo (JP); Toyo Engineering Corp., Tokyo (JP)

( * ) Notice: Subject to any disclaimer, the term of this patent is extended or adjusted under 35 U.S.C. 154(b) by 729 days.

(21) Appl. No.: 11/247,667

(22) Filed: Oct. 11, 2005

(65) Prior Publication Data

US 2006/0217895 A1  Sep. 28, 2006

(30) Foreign Application Priority Data

Mar. 25, 2005  (JP) .............................. 2005-087421

(51) Int. Cl.
*G01N 17/02* (2006.01)
*G01N 3/56* (2006.01)

(52) U.S. Cl. ................................ 436/6; 702/30; 702/34

(58) Field of Classification Search ..................... 436/6; 702/30, 34
See application file for complete search history.

(56) References Cited

U.S. PATENT DOCUMENTS

| 5,656,151 A * | 8/1997 | McLaughlin et al. ........... 208/95 |
| 5,656,152 A * | 8/1997 | McLaughlin et al. ........... 208/95 |
| 6,548,016 B1 * | 4/2003 | Borgard ........................ 422/12 |
| 2002/0016272 A1 * | 2/2002 | Kakizawa et al. ............. 510/175 |
| 2003/0004696 A1 * | 1/2003 | Yamazaki et al. .............. 703/12 |

FOREIGN PATENT DOCUMENTS

| JP | 9-159664 A | 6/1997 |
| JP | 10-221238 A | 8/1998 |

OTHER PUBLICATIONS

Anderko et al., "Electrolyte solutions: from thermodynamic and transport property models to the simulation of industrial processes," Fluid Phase Equilibria 194-197 (2002) 123-142.*
Prevention of Corrosion in Hydrodesulfurizer Air Coolers and Condensers by D. G. Damin and J.D. McCoy from The International Corrosion Forum Devoted Exclusively to the Protection and Performance of Materials dated Mar. 6-10, 1978; Paper No. 131 (7 pages).

* cited by examiner

*Primary Examiner*—Jill Warden
*Assistant Examiner*—Shogo Sasaki
(74) *Attorney, Agent, or Firm*—Flynn, Thiel, Boutell & Tanis, P.C.

(57) ABSTRACT

It is an object to establish a test method that enables a high-concentration ammonium bisulfide environment to be reproduced at a laboratory level, and enables the corrosivity of a material to be evaluated easily and highly accurately. According to the test method, when evaluating the corrosion resistance of a material under an ammonium bisulfide environment, the corrosion resistance of the material is evaluated by simulating the relationship between the ammonium bisulfide concentration of a test solution and the pressure in advance, and then determining the ammonium bisulfide concentration from the pressure.

3 Claims, 6 Drawing Sheets

METHOD OF EVALUATING CORROSION RESISTANCE OF MATERIAL UNDER AMMONIUM BISULFIDE ENVIRONMENT

FIELD OF THE INVENTION

The present invention relates to a test method for evaluating corrosion resistance that facilitates the selection of materials and so on for equipment in an oil refinery or the like where bisulfide and ammonia coexist.

PRIOR ART

In oil refineries, there is a problem of materials corroding under an ammonium bisulfide ($NH_4HS$) environment, which is produced in an environment in which bisulfide and ammonia coexist, for example in hydrodesulfidation equipment.

Ascertaining the corrosion resistance of materials used under such an ammonium bisulfide environment in advance is effective from the viewpoint of selecting materials for equipment, investigating failures due to corrosion, reducing the cost of corrosion prevention management, and so on.

However, a corrosion environment due to ammonium bisulfide produced under the coexistence of bisulfide and ammonia is a high-temperature, high-pressure, high-concentration $NH_4HS$ environment and a deoxidating environment, and simulating such an environment at a laboratory level is difficult; in particular, a solution cannot be sampled while maintaining a high pressure, and hence is thus very difficult to ascertain the $NH_4HS$ concentration under a high-pressure environment.

Hitherto, materials selection and operational management have thus been carried out referring to Paper No. 131 'Prevention of Corrosion in Hydrodesulfurizer Air Coolers and Condensers', the International Corrosion Forum Devoted Exclusively to the Protection of Materials, Mar. 6-10, 1978, which is the only document giving test data on the corrosion of various metallic materials (carbon steel, stainless steel, titanium, aluminum etc. ) under an ammonium bisulfide environment (the relationship between the ammonium bisulfide concentration and the corrosion rate under conditions of a temperature of 93° C. and a pressure of 13.8 MPa).

DISCLOSURE OF THE INVENTION

It is an object of the present invention to establish a test method that enables a high-concentration ammonium bisulfide environment to be reproduced at a laboratory level, and enables the corrosivity of a material to be evaluated easily and highly accurately.

The present inventors carried out intensive studies to attain the above object, and as a result arrived at the present invention upon discovering that when evaluating the corrosion resistance of a material under an ammonium bisulfide environment, if the relationship between the ammonium bisulfide concentration of a test solution and the pressure is simulated in advance, then through this relationship the ammonium bisulfide concentration can be determined accurately from the pressure.

That is, the present invention provides a method of evaluating the corrosion resistance of a material under an ammonium bisulfide environment, which comprises the steps of simulating the relationship between the ammonium bisulfide concentration of a test solution and the pressure in advance, and determining the ammonium bisulfide concentration from the pressure.

DETAILED DESCRIPTION OF THE INVENTION

According to the method of the present invention, the corrosion resistance of a material under an ammonium bisulfide environment can be evaluated easily at a laboratory level, and the corrosion resistance of the material, i.e. (1) the corrosion rate (weight loss) of the material, and (2) the hydrogen embrittlement susceptibility (cracking), can be measured and evaluated accurately. The present invention is thus very effective in selecting materials for equipment used under an ammonium bisulfide environment, investigating accidents due to corrosion (promptly analyzing the cause of accident), reducing the cost of corrosion prevention management, and so on.

Following is a detailed description of the present invention. In the present invention, the relationship between the pressure and the concentration of ammonium bisulfide generated in a test solution containing bisulfide and ammonia is simulated in advance. As the method for doing this, using physical property analysis software by OLI Systems Inc. of the USA, the pressure is calculated from the composition of the solution, and the fluid concentration is calculated from the pressure.

The physical property analysis software used in the present invention is Mixed-Solvent Electrolyte (MSE) Systems by OLI of the USA. Please see Fluid Phase Equilibria 203 (2002) 141-176, "A speciation-based model for mixed-solvent electrolyte systems". The MSE model is a rigorous speciation-based electrolyte thermodynamic model, and involves a method in which the thermodynamic equilibrium reaction in a high-concentration electrolyte solution containing a non-aqueous polar solvent is predicted theoretically using the permittivity of the solvent and the Gibbs free energy of the chemical species. A high-concentration solution differs from a dilute electrolyte environment in that interactions between ions/molecules strongly influence the thermodynamic properties of the chemical species, and hence the reaction equilibrium between the chemical species. That is, due to interactions, the chemical species in the solution exhibit thermodynamic properties and behavior greatly different to those predicted from a condition of infinite dilution. Several methods of analyzing the physical properties of such high-concentration solutions have hitherto been reported; with MSE, a modified Helgerson model is used for predicting the standard state physical properties, an activity coefficient model is used for predicting the excess physical properties, and the Gibbs energy is expressed in terms of the following three contributing terms.
1) Long-range electrostatic term (solvent electrostatic action; LR)
2) Local composition model term (intermolecular interactions; LC)
3) Ionic interaction term (II)

The formula for calculating the Gibbs energy of the high-concentration electrolyte system used in MSE is as follows.

$$\frac{G^{ex}}{RT} = \frac{G^{ex}_{LR}}{RT} + \frac{G^{ex}_{LC}}{RT} + \frac{G^{ex}_{II}}{RT}$$

LR: Debye-Huckel theory coupled with dielectric constant model for mixed solvents
LC: Local composition model (UNIQUAC) for neutral molecule interactions
II: Second viral coefficient expression with ionic strength dependence 1) Solvent electrostatic action (LR)

For LR, the Gibbs energy is calculated from data on the permittivity of the mixed solvent, the molar volume of the mixed substance, the interionic distance, and so on in accordance with Pitzer-Debye-Huckel theory. Several modified theories for the solvent electrostatic action based on Debye-Huckel theory have been proposed, but it is considered to be the Pitzer-Debye-Huckel theory that best agrees with experimental results for high-concentration electrolytes.

2) Local composition model term (LC)

LC represents the intermolecular interactions, and the Gibbs energy is calculated from data on the size of the molecules, the surface area of the molecules, the dipole interaction coefficient, and so on using the UNIQUAC model. The UNIQUAC model has the characteristic feature that accurate calculation is possible with consideration given to the temperature dependence, the size of the molecules in the solution, and so on.

3) Ionic interaction term (II)

II represents the ion-ion and ion-molecule interactions, and the Gibbs energy is calculated with consideration given to the dipole action of the ions.

Using the above Gibbs energies, the activity coefficient for each of the reactive species is calculated from the following formula, and hence the physical properties are calculated thermodynamically.

$$\ln \gamma_k = \frac{\partial}{\partial n_k} \left( \frac{G^{ex}}{RT} \right)_{T,P,n_{j,j \neq k}}$$

In addition, with MSE, with regard to the electrical conductivity, consideration is given to hydronium ions ($H_3O^+$) in the proton migration rate. $H^+$ exists as $H_3O^+$ in an aqueous solution. A proton in a hydronium ion can migrate through a tunneling effect to the negative side of the dipole of an adjacent water molecule, and hence has higher mobility than other ions. With MSE, because consideration is given to hydronium ions, the proton migration rate is given accurately.

Figure 1:
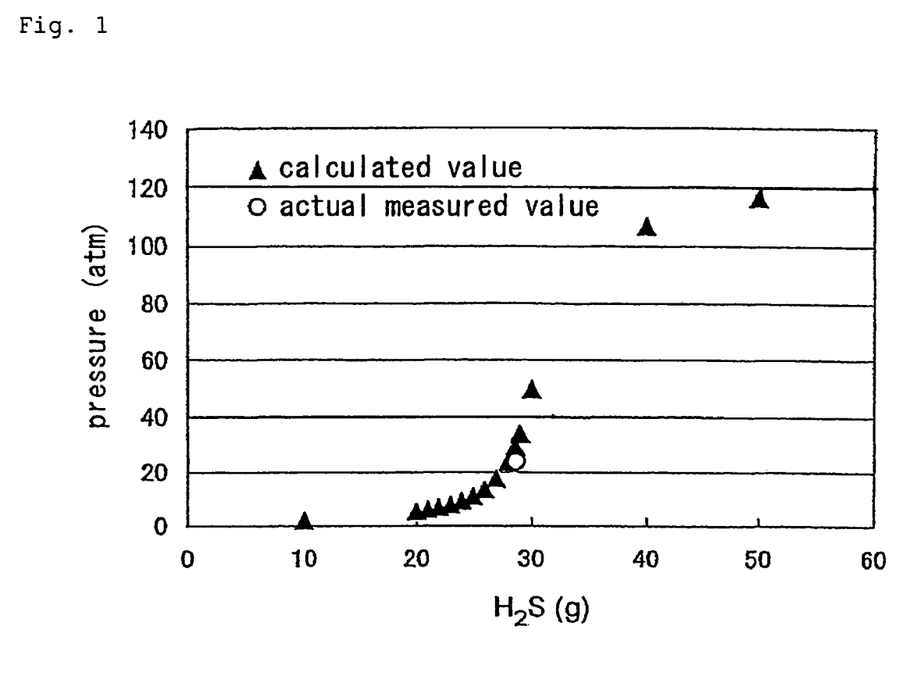
FIG. 1 is a graph of calculated values for the relationship between the concentration (amount) of bisulfide dissolved in ammonia water and the pressure for 30 wt % $NH_4HS$.

Using the above physical property analysis software (MSE), the pressure is calculated from the composition of the solution, and the fluid concentration is calculated from the pressure. Specifically, graphs of calculated values for the relationship between the concentration (amount) of bisulfide dissolved in ammonia water and the pressure are shown in FIG. 1 (30 wt % $NH_4HS$) and FIG. 2 (45 wt % $NH_4HS$). The buildup pressure changes with the concentration of the dissolved bisulfide as in FIGS. 1 and 2. For 45 wt % $NH_4HS$ as in FIG. 2, the molecular weight pressure corresponding to approximately 54 g of bisulfide being dissolved is approximately 44 atm according to theory. If the actual measured value is below this pressure, then this means that the amount of bisulfide dissolved is lower (i.e. the $NH_4HS$ concentration is lower).

Figure 2:
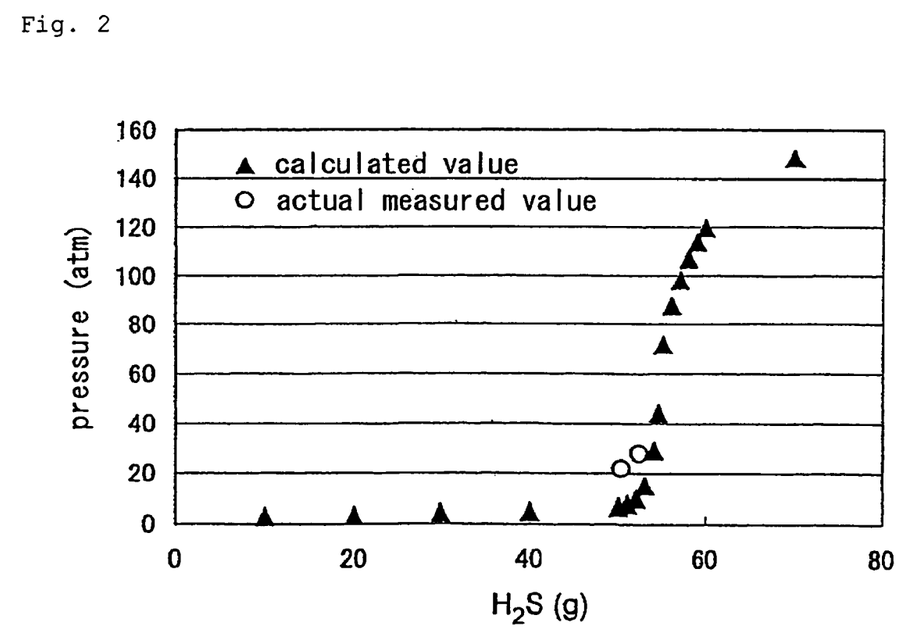
FIG. 2 is a graph of calculated values for the relationship between the concentration (amount) of bisulfide dissolved in ammonia water and the pressure for 45 wt % $NH_4HS$.

Values actually measured using test solutions as described below have been plotted in FIGS. 1 and 2; the actual measured values agree well with the calculated values.

Next, a description will be given of a procedure for preparing a wet ammonium bisulfide solution that is a test solution in the present invention.

(Procedure for Preparing Wet Ammonium Bisulfide Solution)

Figure 3:
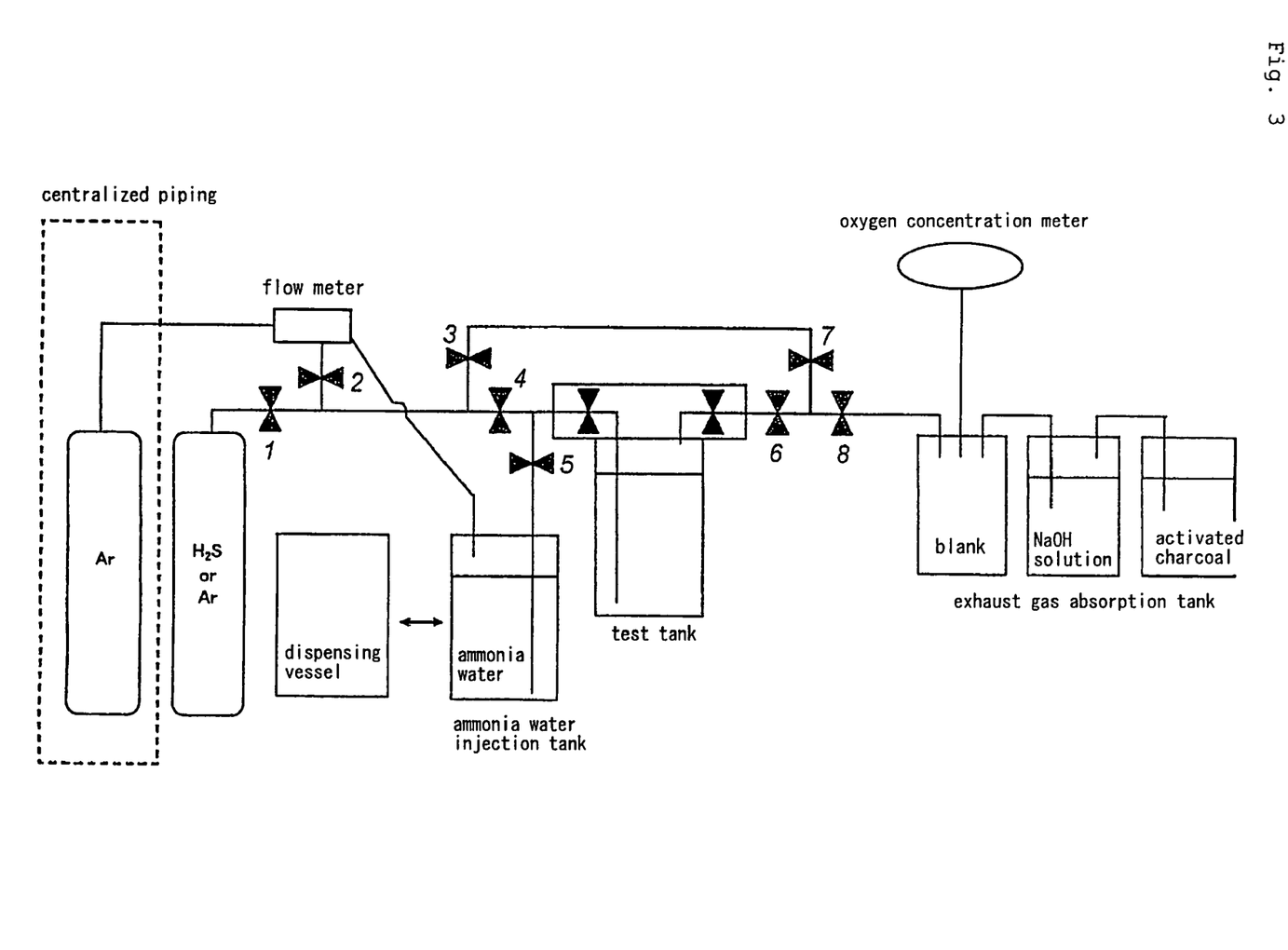
FIG. 3 is a drawing showing a test solution preparing apparatus used in the preparation and evaluation of a wet ammonium bisulfide solution.
Figure 4:
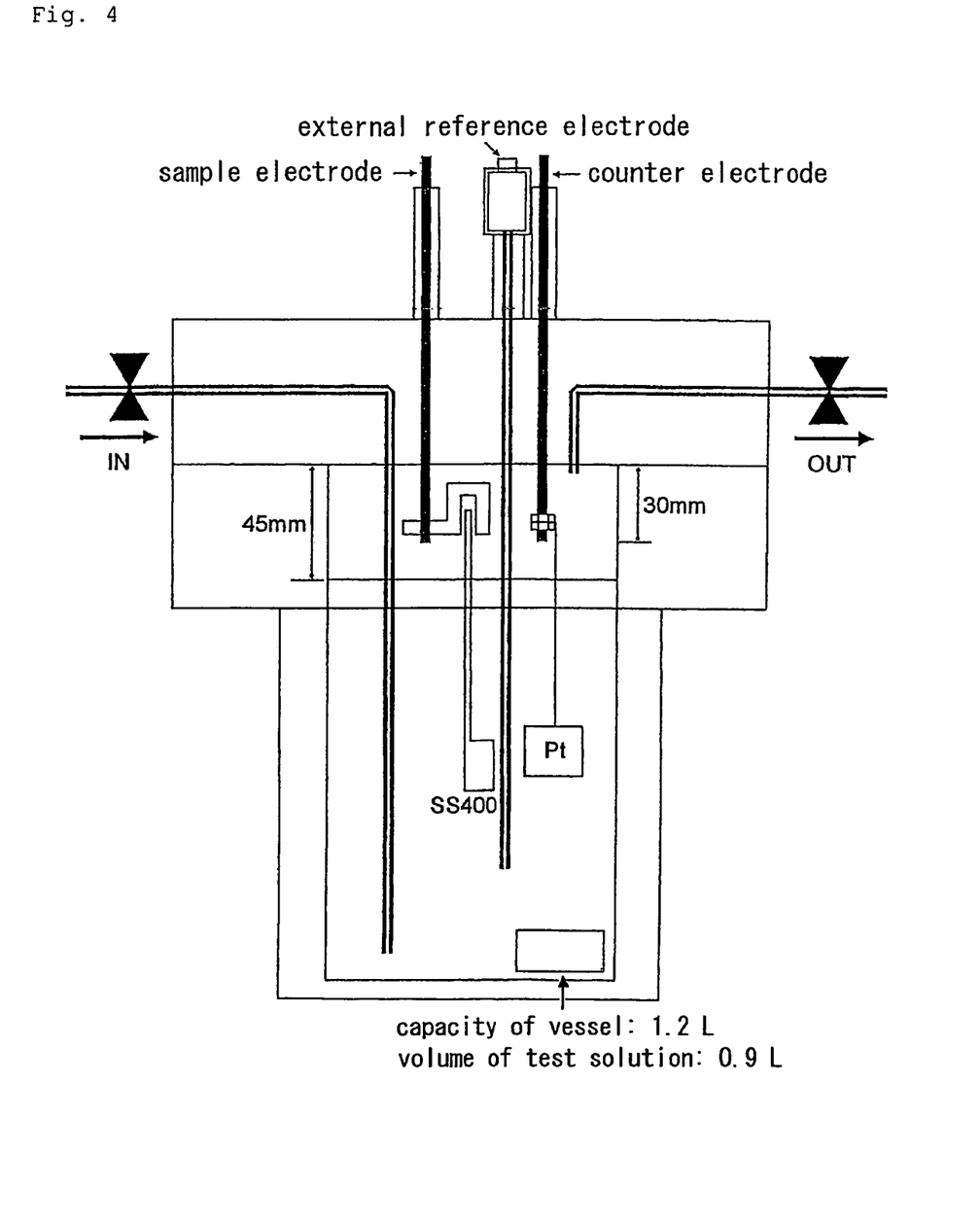
FIG. 4 is a drawing showing the inside of an autoclave test tank of the apparatus of FIG. 3.

(1) A test solution preparing apparatus as shown in FIG. 3 (parts represented by reference numerals 1 to 8 in FIG. 3 are valves) was assembled in the draft in a gas corrosion test chamber, an Ar gas cylinder was connected instead of an $H_2S$ gas cylinder, and the gas tightness of the piping was checked at 0.98 MPa (10 kgf/cm$^2$). After completion of the check, the Ar gas cylinder was changed over to the $H_2S$ gas cylinder, valve 2 was opened, valve 1 was closed, and Ar gas was passed through overnight using centralized piping, thus purging the inside of an autoclave test tank (made by Toshin Kogyo Co., Ltd.) and the piping with Ar gas. It was verified that the oxygen concentration had sufficiently dropped using an oxygen concentration meter (OX100 made by Yokogawa Electric Corporation) installed in an exhaust gas absorption tank. An enlarged drawing of the inside of the autoclave test tank is shown in FIG. 4.

(2) Valve 5 was opened, and 900 ml of 21.8% ammonia water to which 100 ppm of hydrazine had been added was injected into the autoclave test tank from an ammonia water injection tank using Ar gas from a flow meter.

(3) $H_2S$ gas was passed in, and the pressure inside the autoclave test tank was made to be 0.29 MPa (3 kgf/cm$^2$). The valves of the autoclave test tank were closed, and changes in the internal pressure were observed. The internal pressure drops as the $H_2S$ is absorbed by the ammonia water.

$NH_4OH + H_2S \rightarrow NH_4HS \ (NH_4HS + 2H_2O)$ (4) Step (3) was repeated five times, and on the fifth time the pressure was held at 0.29 MPa (3 kgf/cm$^2$) overnight.

(5) High-pressure $H_2S$ gas remaining in the piping was gradually released, and then the inside of the piping was exhausted using. Ar gas.

(6) The autoclave test tank was detached from the piping, and was set in an autoclave boiler next to the GCL, the autoclave test tank was covered with a hood, and a fan was used so as to form an apparatus for which local exhaustion was easy. The autoclave test tank was heated up to 90° C. over 1 hour, and the pressure inside the autoclave test tank was checked, thus ascertaining the ammonium bisulfide concentration, before carrying out an experiment.

The theoretical values (90° C.) were 44 atm for 45 wt % $NH_4HS$, and 29 atm for 30 wt % $NH_4HS$.

(7) After completion of the experiment, the autoclave test tank was cooled down to room temperature, and was then carried over to the GCL, and connected to a filling apparatus.

The ammonia water injection tank was changed over to a sealable dispensing apparatus, and using the pressure inside the test tank, the test solution was gradually jetted out, and thus dispensed into 100 ml FURAN bottles and 500 ml polyethylene bottles in such a way as to not come into contact with the atmosphere (in the case that the internal pressure is insufficient, Ar gas is passed in from the exhaust side using a bypass).

Following is an outline of the preparation of a solution sample for analysis.

(Outline of Preparation of Test Solution Analysis Sample)

5 L of a 200 g/L solution of zinc sulfate heptahydrate and 5 L of a 100 g/L solution of sodium carbonate were prepared in advance for a sulfide ion fixing solution. Approximately 50 mg of sulfide ions can be fixed with 10 ml of a mixture thereof (JIS K0101-39.1 Note 2.). After having cooled down to room temperature, the test tank was carried into the draft in the GCL, and connected to the filling apparatus.

First, the zinc sulfate solution and the sodium carbonate solution that had been prepared were mixed together in equal volumes, thus preparing 10 L of a sulfide ion fixing solution (a suspension of basic zinc carbonate). This solution was prepared by mixing at the time of use. Moreover, upon the mixing, a large amount of precipitate is produced, and hence stirring was carried out well, and was continued using a stirrer or the like so that the precipitate did not settle.

A FURAN bottle into which the solution had been sampled was sunk into the sulfide ion fixing solution and mixing was carried out while taking care not to allow the bisulfide to escape, thus fixing the sulfide ions as zinc sulfide. A sample was taken from the solution into a dispensing vessel A (a 500 ml polyethylene bottle).

(8) For the dispensed solution, the ammonia concentration (distillation/neutralization titration method), the $H_2S$ concentration (hydrochloric acid activation/iodine titration method), and the pH were measured by analyzing the solution in accordance with JIS K0102.

(9) As post-treatment, the test solution remaining in the autoclave test tank was discharged using Ar gas passed in from the exhaust side using a bypass from the ammonia water injection side. At this time, an NaOH solution was put in advance into the vessel into which the test solution was to be discharged, and hence the $H_2S$ was absorbed, and at the same time the high-concentration test solution was diluted. Ar gas was passed in from the centralized piping, thus exhausting $H_2S$ and $NH_3$ remaining in the test tank and the piping. The piping was detached from the autoclave test tank, the lid of the test tank was opened, the remaining test solution was recovered, and the inside of the test tank and the piping was washed with pure water.

As described above, a corrosion environment due to ammonium bisulfide produced under the coexistence of bisulfide and ammonia is a deoxidating environment; as a result of their studies, the present inventors have discovered that when reproducing such an environment, chemical deoxidation treatment using hydrazine is effective for improving the accuracy. Hydrazine was thus added into the ammonia water when preparing the wet ammonium bisulfide solution as described above.

For the wet ammonium bisulfide solution obtained as described above, the corrosion resistance of various metallic materials (the corrosion rate (thinning rate) of the material, and the hydrogen embrittlement susceptibility (cracking)) can be evaluated using a weight reduction method or an electrochemical measurement method. With the weight reduction method, the corrosion rate of the material is calculated from the reduction in weight between before and after a test using a coupon test piece in accordance with JIS K0100 or the like. Moreover, regarding the hydrogen embrittlement susceptibility, the amount of hydrogen in the steel of a coupon test piece that has been inserted into the autoclave test tank in advance is evaluated through measurement using an element-in-metal analyzer. With the electrochemical measurement method, the corrosivity of the environment is evaluated electrochemically from cathodic polarization and anodic polarization measurements, and the corrosion rate is calculated.

Following is a description of the electrochemical measurement method in a high-concentration ammonium bisulfide aqueous solution.

(Outline of Electrochemical Measurement Method in Wet Ammonium Bisulfide Environment)

(1) A filling apparatus that had been disassembled and washed with pure water was assembled. Regarding the packing that is frequently detached at this time, Teflon packing was used rather than metal packing, and the packing was replaced for each batch so as to prevent leakage of gas due to deterioration. Moreover, Teflon rubber packing was packed in at a connecting part between an external reference electrode and a cooling tank. Regarding pressure regulators used at this time, a high-pressure one was used for the Ar gas cylinder, and a hydrogen gas (reverse screw) one was used for the $H_2S$ gas cylinder. Once the assembly had been completed, the gas tightness was checked (with soapy water) at an internal pressure of 5 MPa using the Ar gas for deaerating. To prevent failure of the pressure regulator at this time, valve 1 on the $H_2S$ gas cylinder side was closed in advance.

(2) The test tank was temporarily detached from the filling apparatus, and the external reference electrode was further detached. The external reference electrode was then reassembled. At this time, the Ag/AgCl electrode that has been used in the test will be somewhat corroded, and hence is not reused. Next, the potential difference between the assembled external reference electrode and a standard electrode was checked and recorded, this being because the Ag/AgCl electrode corrodes due to $H_2S$ that gets into the electrode during the test and hence the potential changes.

(3) A weighed flag test piece for electrochemical measurement was ground with emery paper (abrasive paper) until the roughness was #600 immediately in advance, ultrasonic washing was carried out with acetone, and the weighed flag test piece for electrochemical measurement was set in the autoclave test tank and was incorporated into the filling apparatus.

(4) Ar gas was passed in, thus purging the inside of the test tank and the piping with Ar gas. Once Ar gas had been passed in to a certain extent, the passing in of the Ar gas was temporarily stopped, all of the valves were closed in a state in which the internal pressure had been raised to 0.3 MPa, and it was checked that there was no leakage by checking that the internal pressure did not drop upon leaving for 1 hour. If there was no leakage, then Ar gas was passed in overnight at a secondary pressure of approximately 0.2 MPa (estimated flow rate approximately 50 ml/min). It was verified that the oxygen concentration had sufficiently dropped in a state with the flow rate increased to approximately 300 ml/min using an oxygen concentration meter installed in the exhaust gas absorption tank.

(5) Pure water was added to ammonia water in the draft, and the mixture was stirred well. Hydrazine monohydrate was added to the solution using a measuring pipette and the mixture was further stirred, thus preparing ammonia water having hydrazine added thereto. This solution was measured into a 1 L conical flask (graduated), and was incorporated into the ammonia water injection part (care must be taken since ammonia has a high vapor pressure, and hence the solution may jet out when capped with an SUS tube-possessing silicone stopper for injection). The solution was injected into the test tank using Ar gas introduced in from piping branching off from the Ar gas cylinder. When the injection is stopped, valve 5 is first closed, and then the Ar gas is turned off immediately thereafter. If only the gas is turned off, then it may be that the injection does not stop due to residual pressure, and hence some time after closing valve 5 the silicone stopper comes out and the gas jets out.

(6) $H_2S$ gas was gradually passed in, and the pressure inside the test tank was made to be 0.3 MPa. At the start of passing the $H_2S$ gas in, the internal pressure does not rise readily. Care is taken to not blow the gas in all at once, paying attention to noise and vibration.

(7) The valves of the autoclave test tank were closed, and changes in the internal pressure were observed. The internal pressure drops as the $H_2S$ is absorbed by the ammonia water.

$$NH_4OH + H_2S \rightarrow NH_4S-H + H_2O\ (NH_4^+ + HS^{31} + H_2O)$$

Upon repeating the temperature of the solution initially rises to approximately 50° C. through the heat of reaction, and hence care must be taken.

(8) Steps (6) and (7) were repeated (ten to twenty times) at intervals of approximately 15 minutes until a regular time. After that, all of the valves were closed, the autoclave test tank was left in a pressurized state overnight, and then in the morning it was checked that sufficient internal pressure (at least 0.1 MPa) remained, which was taken as meaning that there will be a sufficiently saturated state under normal pressure. Possibly on account of the external reference electrode, the drop in the internal pressure was greater than during preliminary testing. By way of precaution, the internal pressure was thus raised to 0.5 MPa in the morning, and 30 minutes was allowed to elapse, when it was found that the internal pressure dropped by approximately half.

(9) The external reference electrode was filled with the test solution using the pressure inside the autoclave test tank.

(10) High-pressure $H_2S$ gas remaining in the piping was gradually exhausted, such as not to be released in one go and thus be too much to be absorbed in the absorption tank.

(11) The inside of the piping was exhausted using Ar gas. Next, the pressurized state in the test tank was released, returning the inside of the test tank to normal pressure. At this time, care was taken such that gas was not released in one go so as to be too much to be absorbed in the absorption tank, and such that air did not flow back into the autoclave test tank. Next, the valves of the autoclave test tank main body were closed, and $H_2S$ gas remaining in the piping was exhausted using Ar gas.

(12) The test tank (electrode-possessing autoclave) was detached from the piping, and was set in an autoclave boiler.

(13) As a countermeasure against $H_2S$ leakage, the autoclave was covered with a hood, and exhausting to the outside was carried out using a fan-possessing duct, thus forming an apparatus for which local exhaustion was easy.

(14) A potentiostat was connected to the autoclave test tank, and the immersion potential of the electrochemical measurement test piece at room temperature was measured.

(15) The autoclave was heated up to 90° C. over approximately 1.5 hours, and this temperature was held while checking the pressure inside the autoclave. Changes with time in the potential and the temperature were recorded using a data logger during the heating and while the temperature was being held.

The theoretical values (90° C.) were 4.5 MPa for 45 wt % $NH_4HS$, and 3.0 MPa for 30 wt % $NH_4HS$.

(16) Changes in the immersion potential were observed for approximately 2 hours, and then cathodic polarization was carried out, the immersion potential after the measurement was checked, and then anodic polarization was carried out (sweep rate 10 mV/min).

(17) After completion of the test, the autoclave test tank was allowed to cool down sufficiently and was then carried over to the GCL, and connected to the filling apparatus.

(18) Ar gas was passed in, thus exhausting $H_2S$ and $NH_3$ remaining in the test tank and the piping.

(19) The piping was detached from the test tank, the test tank was moved to a test site, and the lid of the autoclave test tank was opened and the test piece was taken out. There will be much $H_2S$ remaining inside, and hence the work was carried out wearing a gas mask. After being taken out, the test piece was washed with pure water and then dried, and the weight was measured, and a photograph of the external appearance was taken.

(20) The potential difference between the external reference electrode removed from the autoclave test tank and the standard electrode used in (1) was checked, thus checking the state of deterioration of the electrode.

Figure 5:
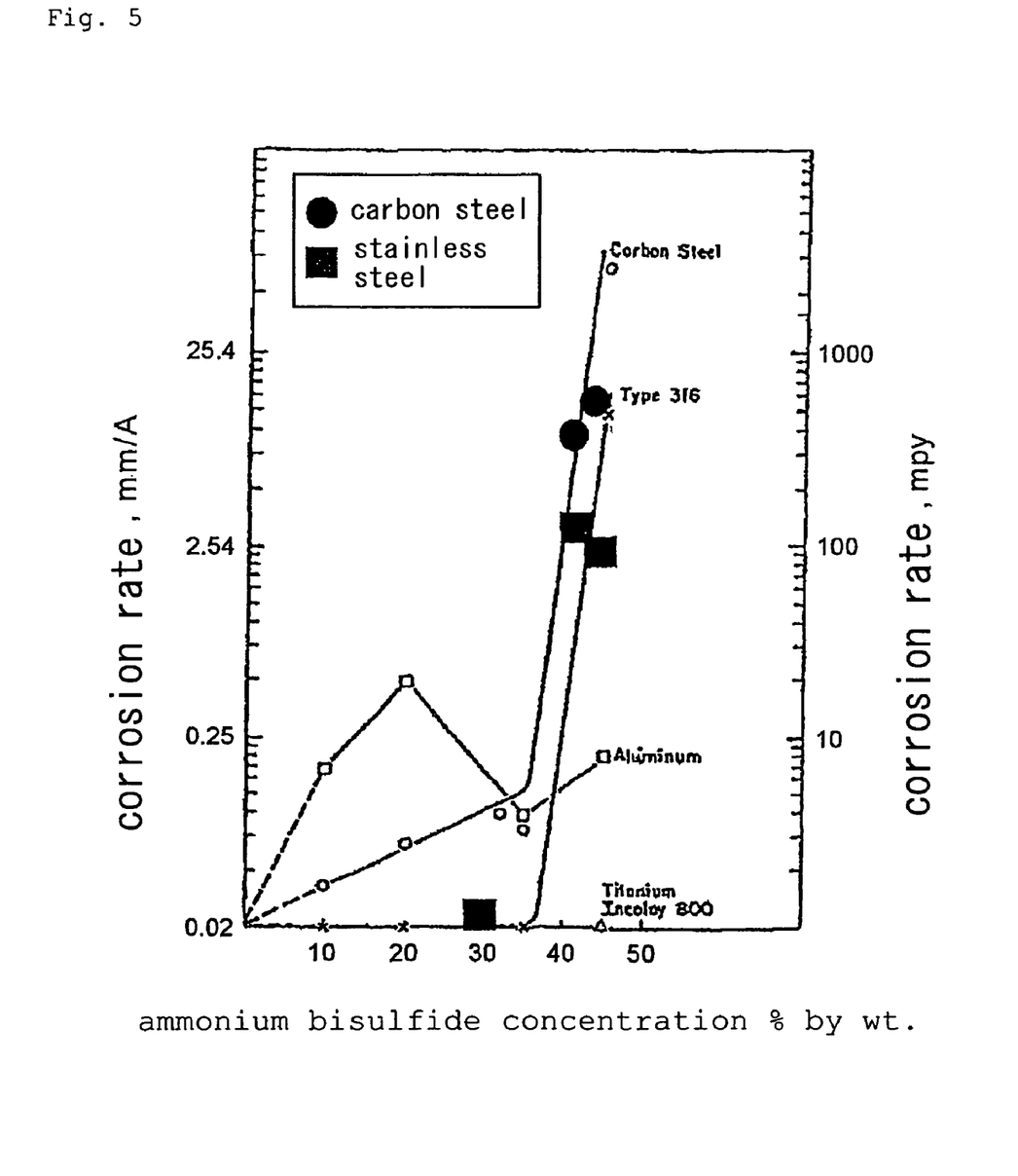
FIG. 5 is a graph showing the relationship between the $NH_4HS$ concentration and the corrosion rate for carbon steel and stainless steel (type 316) superimposed in Paper No. 131 'Prevention of Corrosion in Hydrodesulfurizer Air Coolers and Condensers', the International Corrosion Forum Devoted Exclusively to the Protection of Materials, Mar. 6-10, 1978.

Upon measuring the corrosion rates of carbon steel and stainless steel (type 316) in a 40% $NH_4HS$ aqueous solution as in previously mentioned Paper No. 131 'Prevention of Corrosion in Hydrodesulfurizer Air Coolers and Condensers', the International Corrosion Forum Devoted Exclusively to the Protection of Materials, Mar. 6-10, 1978 in this way, as shown in FIG. 5, approximately the same results as in FIG. 1 in Paper No. 131 'Prevention of Corrosion in Hydrodesulfurizer Air Coolers and Condensers', the International Corrosion Forum Devoted Exclusively to the Protection of Materials, Mar. 6-10, 1978 were obtained.

Figure 6:
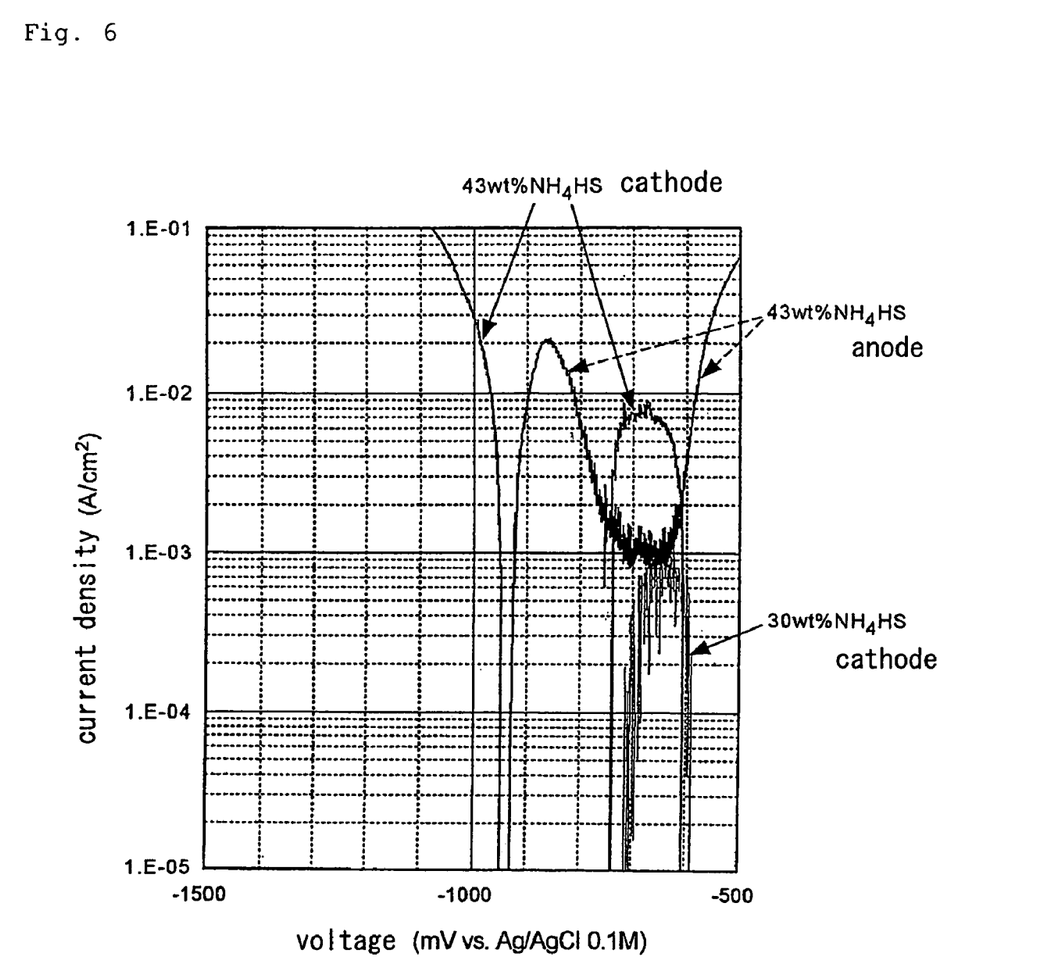
FIG. 6 is a graph showing an example of measuring polarization curves for carbon steel in high-concentration ammonium bisulfide environments.

Moreover, an example of measuring polarization curves for carbon steel in high-concentration ammonium bisulfide environments is shown in FIG. 6. From the polarization measurement results, it can be seen that carbon steel in a high-concentration ammonium bisulfide environment is in a state such that transition readily occurs between a passive region (a region of low corrosivity) around approximately −700 mV (Ag/AgCl) and an active region (a region of high corrosivity) around approximately −900 mV (Ag/AgCl).

Figure 7:
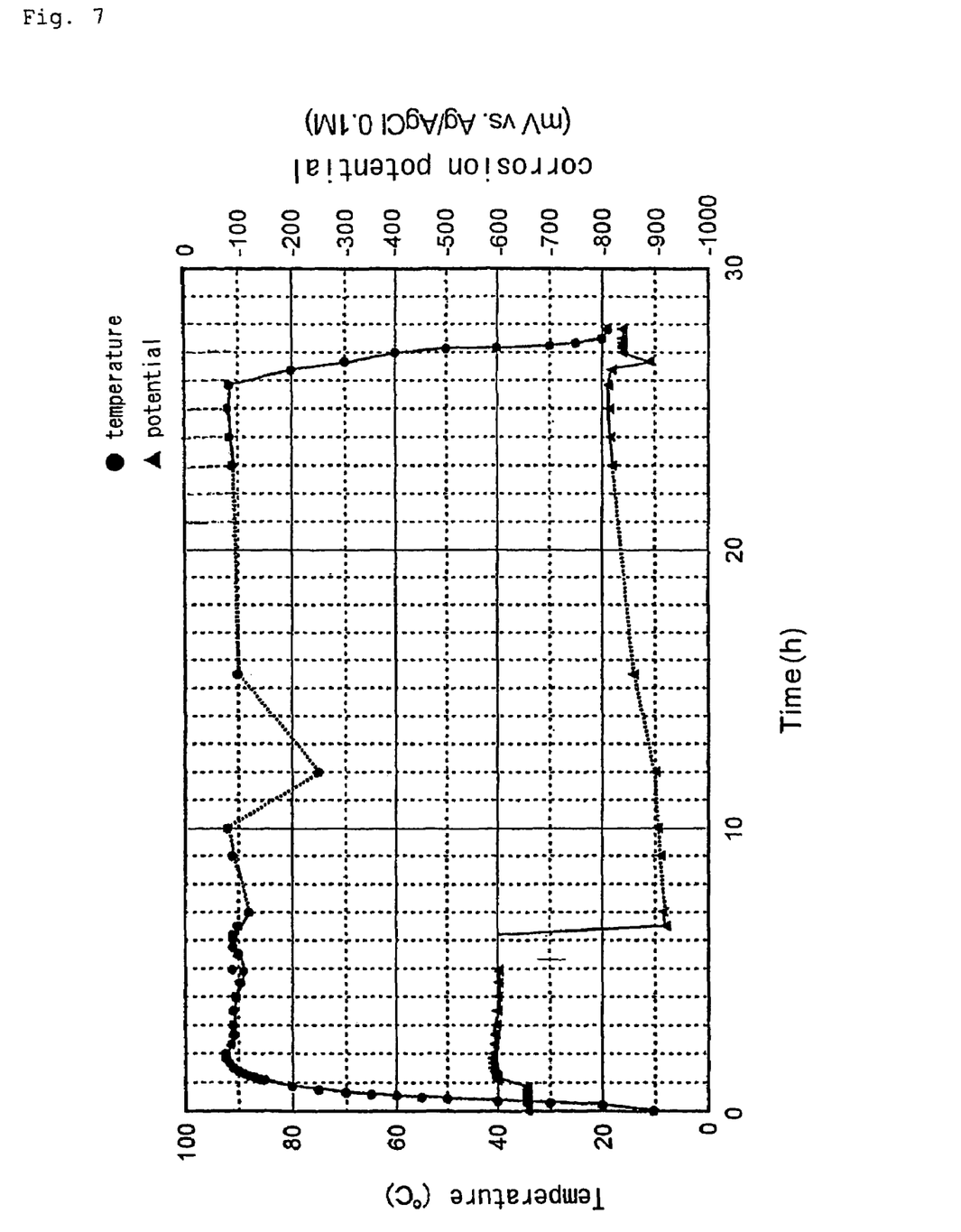
FIG. 7 is a graph showing an example of measuring changes over time in the corrosion potential for carbon steel at a concentration of approximately 45 wt % $NH_4HS$.

Moreover, FIG. 7 shows an example of measuring changes over time in the corrosion potential for carbon steel at a concentration of approximately 45 wt %. In this test, the corrosion rate of the carbon steel was high, but the corrosion potential of the carbon steel in this environment was −900 mV (Ag/AgCl). It can thus be seen that in this environment in which severe corrosivity was observed, the carbon steel was in the active region.

In this way, it can be seen that regarding corrosivity in an ammonium bisulfide environment, even if the corrosivity in the passive region is low, it is conjectured that transition into the active region will occur readily upon changes in conditions such as the concentration or temperature, and hence to accurately ascertain the corrosion resistance of a material, it is important to carry out a corrosion test after accurately ascertaining the concentration and the temperature.

Furthermore, the present invention can also be applied as a method of evaluating a corrosion environment using simulation of a high-concentration electrolyte; one example of such an application is sulfuric acid dew point corrosion, which is a problem with boiler flue gas systems. Sulfuric acid dew point corrosion is corrosion due to sulfuric acid that occurs in low-temperature parts of equipment in which sulfur oxides are contained in flue gas such as heavy oil-burning boilers; this is influenced by the temperature of metal surfaces, the combustion gas composition (mainly $SO_3$), and the dew point temperature of the gas. If sulfur (S) is contained in a fuel, then sulfur dioxide ($SO_2$) is produced upon combustion, and if this is further oxidized then anhydrous sulfuric acid (sulfur trioxide, $SO_3$) is formed. Sulfuric acid has a high dew point temperature due to moisture, and hence a high-concentration sulfuric acid environment is produced at high temperature and thus corrosion occurs. If the temperature drops, then sulfuric acid solutions of various concentrations are produced through moisture from water vapor, and these corrode materials; according to the present invention, reproduction of such corrosion environments and evaluation thereof are easy.

The invention claimed is:

1. A method of evaluating the corrosion resistance of a material in an ammonium bisulfide environment, which comprises the steps of:

simulating, using physical property software, a relationship between a pressure and a concentration of an ammonium bisulfide test solution in advance to calculate a desired pressure of said test solution needed in the corrosion resistance evaluation;

preparing a wet ammonium solution containing hydrazine;

preparing a filling apparatus comprising an autoclave test tank with a pressure regulator;

setting a test piece in the autoclave test tank;

injecting the wet ammonium solution containing hydrazine into the autoclave test tank;

passing hydrogen sulfide gas into said autoclave test tank to prepare said ammonium bisulfide test solution and maintaining the autoclave test tank at said desired pressure;

heating the autoclave test tank at a desired temperature;

holding the desired temperature of the autoclave test tank and checking the internal pressure of the autoclave;

measuring the temperature of the autoclave test tank;

determining the ammonium bisulfide concentration from the internal pressure; and measuring the change in the weight of the test piece.

2. The method of claim 1, wherein a high-concentration electrolyte is simulated.

3. The method of claim 1 wherein the change in weight of the test piece is measured by a weight reduction method or an electrochemical measurement method.

* * * * *